US012337179B2

(12) United States Patent
Annecchino et al.

(10) Patent No.: US 12,337,179 B2
(45) Date of Patent: Jun. 24, 2025

(54) STIMULATION TARGETING AND CALIBRATION FOR ENHANCED SURROUND INHIBITION RECRUITMENT IN SPINAL CORD STIMULATION THERAPY (71) Applicant: Boston Scientific Neuromodulation Corporation, Valencia, CA (US)

(72) Inventors: Luca A. Annecchino, London (GB); Que Doan, West Hills, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 420 days.

(21) Appl. No.: 18/045,736

(22) Filed: Oct. 11, 2022

(65) Prior Publication Data

US 2023/0121243 A1 Apr. 20, 2023

Related U.S. Application Data

(60) Provisional application No. 63/262,726, filed on Oct. 19, 2021.

(51) Int. Cl.
*A61N 1/36* (2006.01)
*A61N 1/05* (2006.01)

(52) U.S. Cl.
CPC ..... *A61N 1/36071* (2013.01); *A61N 1/36062* (2017.08); *A61N 1/0551* (2013.01)

(58) Field of Classification Search
CPC ............ A61N 1/36071; A61N 1/36062; A61N 1/0551; A61N 1/36132; A61N 1/3615; A61N 1/0553
See application file for complete search history.

(56) References Cited

U.S. PATENT DOCUMENTS

| 6,181,969 | B1 | 1/2001 | Gord |
| 6,516,227 | B1 | 2/2003 | Meadows et al. |
| 8,180,445 | B1 | 5/2012 | Moffitt |
| 8,606,362 | B2 | 12/2013 | He et al. |
| 8,620,436 | B2 | 12/2013 | Parramon et al. |
| 9,259,574 | B2 | 2/2016 | Aghassian et al. |
| 2003/0204222 | A1 | 10/2003 | Leinders et al. |
| 2013/0289665 | A1 | 10/2013 | Marnfeldt et al. |
| 2015/0080982 | A1 | 3/2015 | Funderburk |
| 2015/0157861 | A1 | 6/2015 | Aghassian |

(Continued)

FOREIGN PATENT DOCUMENTS

| WO | 2020/163037 A1 | 8/2020 |
| WO | 2021/178105 | 9/2021 |

OTHER PUBLICATIONS

International Search Report and Written Opinion regarding corresponding PCT Application No. PCT/US2022/077915, mailed Feb. 6, 2023.

(Continued)

*Primary Examiner* — Paula J Stice
(74) *Attorney, Agent, or Firm* — Lewis & Reese, PLLC (57) ABSTRACT

Methods and systems for providing electrical stimulation to a patient's spinal cord using electrode leads implanted in the patient's spinal column are described. Embodiments involve biphasic stimulation where during a first phase a first pole provides stimulation to a first location and during a second phase a second pole provides stimulation to a second location. The two phases may have the same or different amplitudes. The amplitudes of the two phases may be determined based on perception thresholds for stimulation at the two locations.

18 Claims, 9 Drawing Sheets

(56) References Cited

U.S. PATENT DOCUMENTS

| | | |
|---|---|---|
| 2015/0231402 A1 | 8/2015 | Aghassian |
| 2015/0360038 A1 | 12/2015 | Zottola et al. |
| 2018/0071520 A1 | 3/2018 | Weerakoon et al. |
| 2018/0071527 A1 | 3/2018 | Feldman et al. |
| 2018/0140831 A1 | 5/2018 | Feldman et al. |
| 2019/0083796 A1 | 3/2019 | Weerakoon et al. |
| 2019/0091477 A1 | 3/2019 | Kallmyer |
| 2020/0061380 A1 | 2/2020 | Zhang et al. |
| 2020/0147390 A1 | 5/2020 | Zhang et al. |

OTHER PUBLICATIONS

Hillman, P., et al., "Inhibitory and Excitatory Factors Influencing the Receptive Fields of Lamina 5 Spinal Cord Cells," Exp. Brain Res., 9, 284-306, 1969.

Melzack, Ronald, et al., "Pain Mechanisms: A New Theory," Science, vol. 150, No. 3699, Nov. 19, 1965, pp. 971-979.

Zhang, Tianhe C., et al., "Modeling Effects of Spinal Cord Stimulation on Wide-Dynamic Range Dorsal Horn Neurons: Influence of Stimulation Frequency and GABAergic Inhibition," J. Neurophysiol., 115, pp. 552-567, 2014.

STIMULATION TARGETING AND CALIBRATION FOR ENHANCED SURROUND INHIBITION RECRUITMENT IN SPINAL CORD STIMULATION THERAPY

CROSS REFERENCE TO RELATED APPLICATIONS

This is a non-provisional of U.S. Provisional Patent Application Ser. No. 63/262,726, filed Oct. 19, 2021, to which priority is claimed, and which is incorporated herein by reference.

FIELD OF THE INVENTION

This application relates to Implantable Medical Devices (IMDs), generally, Spinal Cord Stimulators, more specifically, and to methods of control of such devices.

INTRODUCTION

Implantable neurostimulator devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability with any implantable neurostimulator device system.

Figure 1:
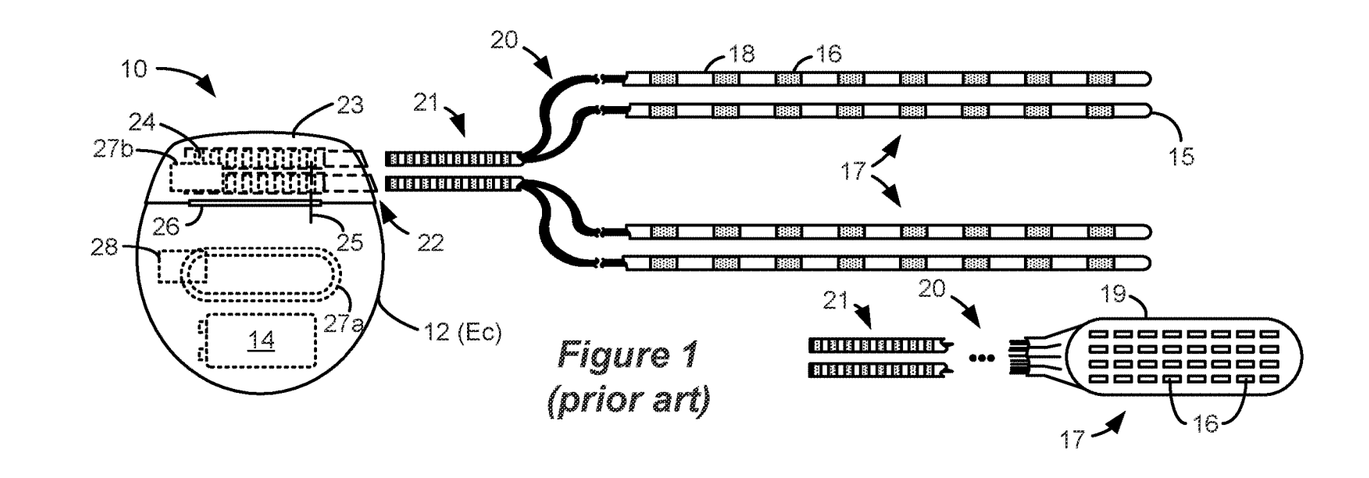
FIG. 1 shows an Implantable Pulse Generator (IPG) useable for Spinal Cord Stimulation (SCS), in accordance with the prior art.

An SCS system typically includes an Implantable Pulse Generator (IPG) 10 shown in FIG. 1. The IPG 10 includes a typically conductive biocompatible device case 12 that holds the IPG's circuitry and a battery 14 for providing power for the IPG to function. The IPG 10 is coupled to tissue-stimulating electrodes 16 via one or more electrode leads that form an electrode array 17. For example, one or more percutaneous leads 15 can be used having ring-shaped or split-ring electrodes 16 carried on a flexible body 18. In another example, a paddle lead 19 provides electrodes 16 positioned on one of its generally flat surfaces. Lead wires 20 within the leads are coupled to the electrodes 16 and to proximal contacts 21 insertable into lead connectors 22 fixed in a header 23 on the IPG 10, which header can comprise an epoxy for example. Once inserted, the proximal contacts 21 connect to header contacts 24 within the lead connectors 22, which are in turn coupled by feedthrough pins 25 through a case feedthrough 26 to stimulation circuitry 28 within the case 12.

In the illustrated IPG 10, there are thirty-two electrodes (E1-E32), split between four percutaneous leads 15, or contained on a single paddle lead 19, and thus the header 23 may include a 2×2 array of eight-electrode lead connectors 22. However, the type and number of leads, and the number of electrodes, in an IPG is application specific and therefore can vary. The conductive case 12 can also comprise an electrode (Ec). In a SCS application, the electrode lead(s) are typically implanted in the spinal column proximate to the dura in a patient's spinal cord, preferably spanning left and right of the patient's spinal column. The proximal contacts 21 are tunneled through the patient's tissue to a distant location such as the buttocks where the IPG case 12 is implanted, at which point they are coupled to the lead connectors 22. In other IPG examples designed for implantation directly at a site requiring stimulation, the IPG can be lead-less, having electrodes 16 instead appearing on the body of the IPG 10 for contacting the patient's tissue. The IPG lead(s) can be integrated with and permanently connected to the IPG 10 in other solutions. The goal of SCS therapy is to provide electrical stimulation from the electrodes 16 to alleviate a patient's symptoms, such as chronic back pain.

IPG 10 can include an antenna 27a allowing it to communicate bi-directionally with a number of external devices used to program or monitor the IPG, such as a hand-held patient controller or a clinician's programmer described later with respect to FIG. 5. Antenna 27a as shown comprises a conductive coil within the case 12, although the coil antenna 27a can also appear in the header 23. When antenna 27a is configured as a coil, communication with external devices preferably occurs using near-field magnetic induction. IPG 10 may also include a Radio-Frequency (RF) antenna 27b. In FIG. 1, RF antenna 27b is shown within the header 23, but it may also be within the case 12. RF antenna 27b may comprise a patch, slot, or wire, and may operate as a monopole or dipole. RF antenna 27b preferably communicates using far-field electromagnetic waves, and may operate in accordance with any number of known RF communication standards, such as Bluetooth, Zigbee, MICS, and the like.

Figure 2A:
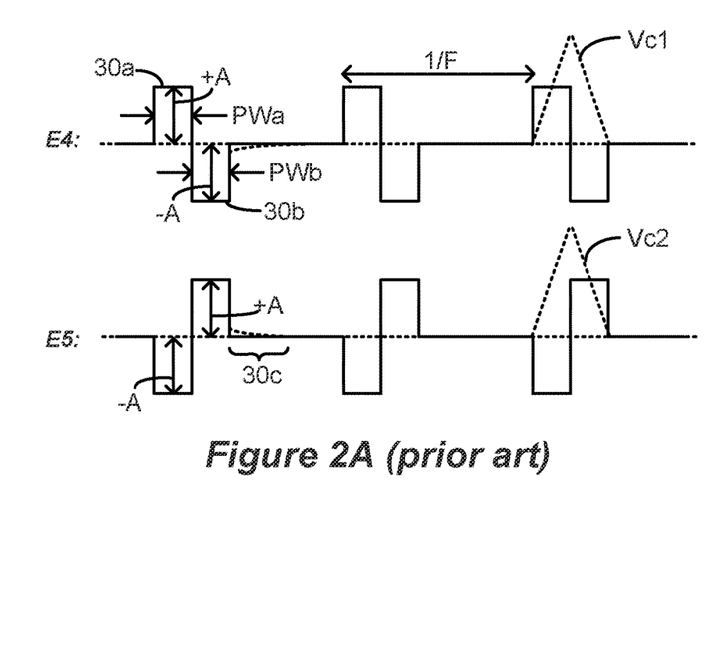
FIGS. 2A and 2B show examples of stimulation pulses producible by the IPG employing active charge recovery and passive charge recovery respectively, in accordance with the prior art.
Figure 2B:
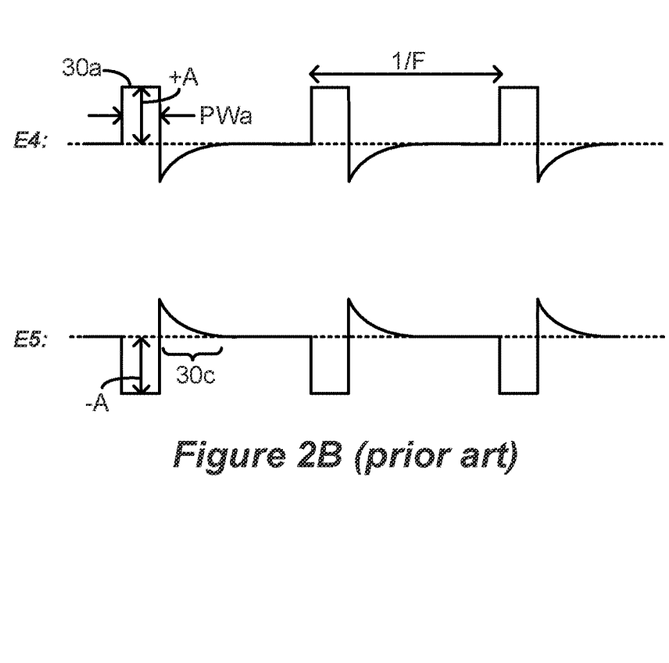

Stimulation in IPG 10 is typically provided by pulses, as shown in FIGS. 2A and 2B. Stimulation parameters typically include the amplitude of the pulses (A; whether current or voltage); the frequency (F) of the pulses; the pulse width (PW) of the pulses (or its individual phases as described below); the electrodes 16 (E) activated to provide such stimulation; and the polarity (P) of such active electrodes, i.e., whether active electrodes are to act as anodes that source current to the tissue or cathodes that sink current from the tissue. These and possibly other stimulation parameters taken together comprise a stimulation program that the IPG 10 can execute to provide stimulation to a patient.

Figure 3:
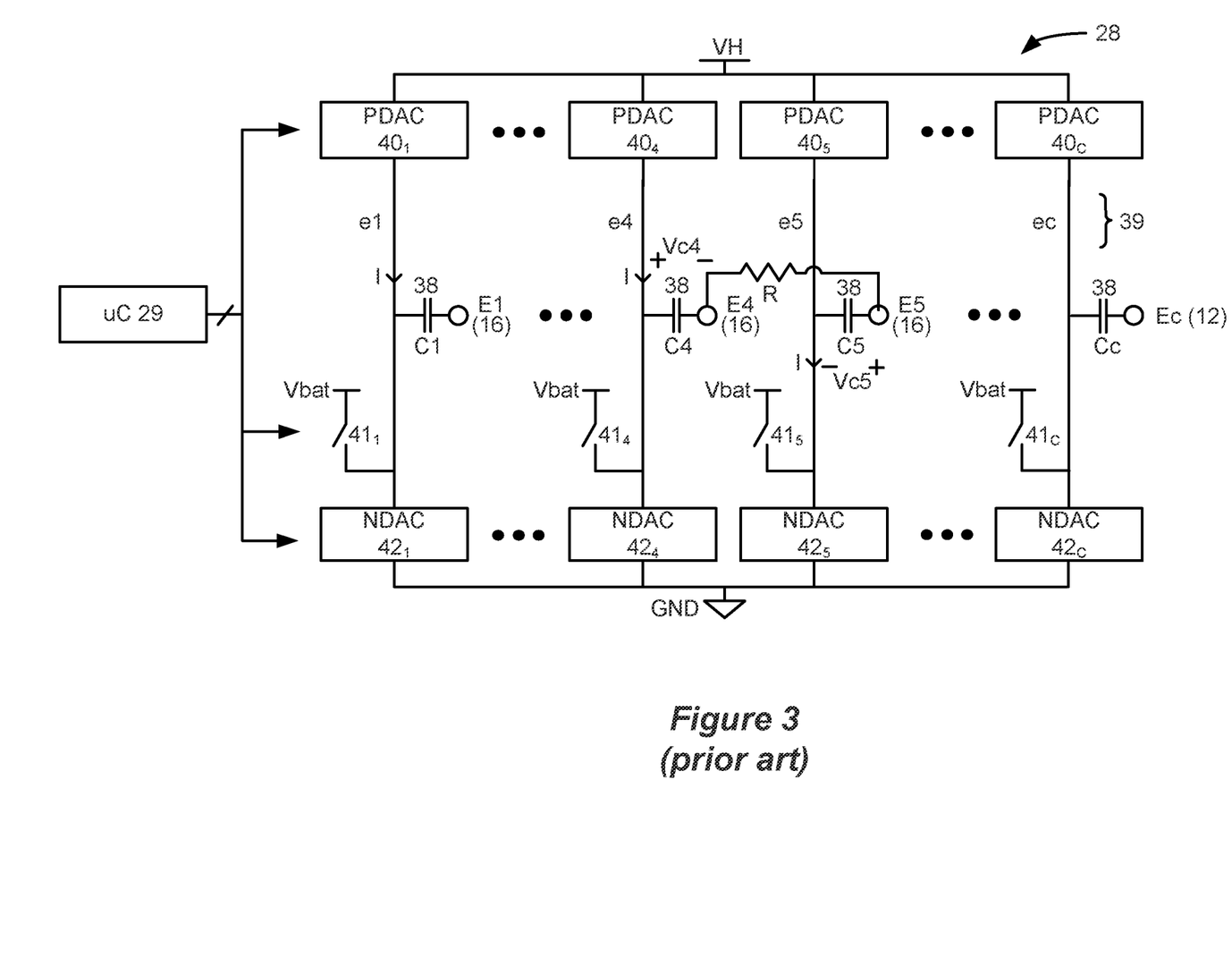
FIG. 3 shows stimulation circuitry used in the IPG to provide stimulation pulses, in accordance with the prior art.

The pulses in FIG. 2A comprise two pulse phases 30a and 30b each actively driven by stimulation circuitry 28 shown in FIG. 3. During the first phase 30a, electrode E4 has been selected as an anode and thus sources a positive current of amplitude +A to the tissue, while electrode E5 has been selected as a cathode and thus sinks a corresponding negative current of amplitude −A from the tissue. However, more than one electrode may act as an anode at a given time, and more than one electrode may act as a cathode at a given time. Stimulation may also occur using the case electrode Ec, as shown in FIG. 3.

The pulses as shown in FIG. 2A, with two actively-driven phases 30a and 30b, are typically known as "biphasic" pulses, with phases 30a and 30b having opposite polarity. (A short interphase period may intervene between the two phases 30a and 30b during which no current flows, as described below, although this isn't shown). The use of biphasic pulses are useful in charge recovery, which can be necessary in light of capacitances in the current path established between the selected electrodes, as explained further below. Although not shown, each of the phases 30a and 30b could be broken up into a series of higher-frequency pulses, which is often referred to as a "burst" of pulses, as is well known.

The stimulation circuitry 28 as shown in FIG. 3 includes one or more current source circuits 40, and one or more current sink circuits 42$_i$. The sources and sinks 40, and 42, can comprise Digital-to-Analog converters (DACs), and may be referred to as PDACs 40, and NDACs 42, in accordance with the Positive (sourced, anodic) and Negative (sunk, cathodic) currents they respectively issue. In the example shown, a NDAC/PDAC 40$_i$/42$_i$ pair is dedicated (hardwired) to a particular electrode node ei 39. Each electrode node ei 39 is connected to an electrode Ei 16 via a DC-blocking capacitor Ci 38, for the reasons explained below. The stimulation circuitry 28 in this example also supports selection of the conductive case 12 as an electrode (Ec 12), which case electrode is typically selected for monopolar stimulation. PDACs 40, and NDACs 42, can also comprise voltage sources. Although not shown, switching matrices can intervene between the one or more PDACs 40, and the electrode nodes ei 39, and between the one or more NDACs 42, and the electrode nodes. Switching matrices allows one or more of the PDACs or one or more of the NDACs to be connected to one or more anode or cathode electrode nodes at a given time.

The stimulation circuitry 28 is configured by the stimulation parameters, which may be provided to the stimulation circuitry 28 by controller circuitry 29 in the IPG 10. Controller circuitry 29 may comprise a microcontroller, microprocessor, microcomputer, an FPGA, other digital logic structures, etc., which is capable of executing instructions an electronic device. Controller circuitry 29 may comprise a separate component, or may be integrated with an Application Specific Integrated Circuit (ASIC) that includes the stimulation circuitry 28 as well as other circuitry necessary to operate various function of the IPG 10. Proper control of the PDACs 40, and NDACs 42, via the stimulation parameters allows any of the electrodes 16 to act as anodes or cathodes to create a current I of the prescribed amplitude A through a patient's tissue, R, hopefully with good therapeutic effect. In the example shown, and during the first phase 30a in which electrodes E4 and E5 are selected as an anode and cathode respectively, PDAC 40$_4$ and NDAC 42$_5$ are activated and digitally programmed to produce the desired current, A, with the correct timing (e.g., in accordance with the prescribed frequency F and pulse width PWa). During the second phase 30b (PWb), PDAC 40$_5$ and NDAC 42$_4$ would be activated to reverse the polarity of the current. More than one anode electrode and more than one cathode electrode may be selected at one time, and thus current can flow through the tissue R between two or more of the electrodes 16. Power for the stimulation circuitry 28 is provided by a compliance voltage VH, as described in further detail in U.S. Patent Application Publication 2013/0289665. Other examples of stimulation circuitries and details of various PDAC and NDAC circuits are disclosed in U.S. Pat. Nos. 6,181,969, 8,606,362, 8,620,436, U.S. Patent Application Publications 2018/0071520 and 2019/0083796. Note that the stimulation circuitry 28 is capable of independently setting the current at any of the electrodes—what is sometimes known as a Multiple Independent Current Control (MICC).

A DC-blocking capacitor Ci 38 is placed in series between each of the electrode nodes ei 39 and the electrodes Ei 16 (including the case electrode Ec 12). The DC-blocking capacitors 38 act as a safety measure to prevent DC current injection into the patient, as could occur for example if there is a circuit fault in the stimulation circuitry 28. The DC-blocking capacitors 38 are typically provided off-chip (off of the ASIC(s)), and instead may be provided in or on a circuit board in the IPG 10 used to integrate its various components, as explained in U.S. Patent Application Publication 2015/0157861.

As noted above, biphasic pulses as shown in FIG. 2A can be useful to recover charge stored on capacitances in the current path and in particular on the DC-blocking capacitors 38. When constant current I is driven during the first phase 30a, the capacitors in the current path (C4 and C5) will store charge at a rate $dV/dt=I/C$, and thus building a voltage across these capacitors (Vc4 and Vc5). When the polarity of this current is reversed during the second phase 30b, this stored charge is recovered, and the voltage across the capacitors preferably returns to zero before the issuance of the next pulse (i.e., before the next phase 30a). Using biphasic pulses in this manner is sometimes referred to as "active" charge recovery, because the charge stored during the first phase 30a is recovered by a current actively driven by the stimulation circuitry 28 during the second phase 30b. It is usually preferred during active charge recovery that the phases 30a and 30b are charge balanced—that is, that the amount of charge passed during the first phase 30a equal the amount of charge passed during the second phase 30b. This can be achieved by setting the current amplitude and the pulse widths to equal values during both phases (|+A|=|−A|; PWa=PWb). However, this is not strictly necessary, and charge balancing can also be achieved if the product of the amplitude and pulse width is equal for both phases (or more generally if the area under their curves is equal).

Stimulation pulses may also be provided using monophasic pulses followed by the use of passive charge recovery, as shown in FIG. 2B. Such monophasic pulses comprise only a single active phase 30a, which is actively driven as before. Because this phase 30a will charge capacitances in the current path as just described, it is again prudent to recover such charge, but this occurs passively without the stimulation circuitry 28 (i.e., the PDACs and NDACs) driving an active current. Specifically, passive charge recovery switches 41, are provided in the stimulation circuitry 28 (FIG. 3). A switch 41, is coupled between each of the electrode nodes ei 39 and a reference potential. In the depicted example, this reference potential comprises the voltage of the battery 14 (Vbat), although another reference potential can be used. After the first pulse phase 30a is issued, one or more of these switches 41$_i$ (all, or at least 41$_4$ and 41$_5$ whose electrodes nodes e4 and e5 were involved in providing the current during the first phase) are closed during a passive charge recovery period 30c (FIG. 2B). This places the capacitors charged during the first phase in parallel between the reference potential (Vbat), and the patient's tissue, R. As a result, and as shown in FIG. 2B, a current pulse of opposite polarity will flow at each electrode as the capacitors discharge, which current will exponentially decay at a rate depending of the values of the capacitances and the resistances inherent in the IPG's circuitry and the tissue R. Preferably, switches 41, are closed during period 30c for a duration sufficient to effectively recover all charge that was stored on capacitive elements (e.g., capacitors 38) during the first phase 30a. At the end of passive charge recovery period, the switches 41, can again be opened. Passive charge recovery is more fully explained in U.S. Patent Application Publications 2018/0071527 and 2018/0140831.

Note that passive charge recovery can also be used with the biphasic pulses shown in FIG. 2A. Thus, a passive charge recovery period 30c may follow the second actively-driven phase 30b. Even if the actively-driven phases 30a and 30b are designed to be charge balanced, non-idealities may not result in perfect charge balancing, and so providing passive charge recovery during phase 30c can be prudent to assure that charge is fully recovered before the issuance of a next pulse. Examples of active, passive, and combined active-passive charge recovery are discussed in more detail below.

Figure 4:
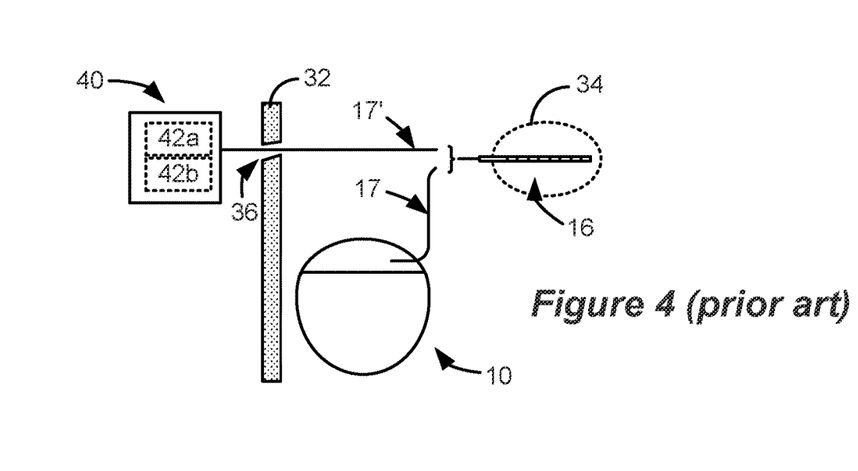
FIG. 4 shows an External Trial Stimulator (ETS) useable to provide stimulation before implantation of an IPG, in accordance with the prior art.

FIG. 4 shows an external trial stimulation environment that may precede implantation of an IPG 10 in a patient. During external trial stimulation, stimulation can be tried on a prospective implant patient without going so far as to implant the IPG 10. Instead, a trial electrode array 17' comprising one or more leads (e.g., one or more percutaneous leads 15 or paddle leads 19) are implanted in the patient's tissue 32 at a target location 34, such as within the spinal column as explained earlier. The proximal ends of the leads of the trial electrode array 17' exit an incision 36 and are connected to an External Trial Stimulator (ETS) 40. The ETS 40 generally mimics operation of the IPG 10, and thus can provide stimulation pulses to the patient's tissue as explained above. See, e.g., 9,259,574, disclosing a design for an ETS. The ETS 40 is generally worn externally by the patient for a short while (e.g., two weeks), which allows the patient and his clinician to experiment with different stimulation parameters to try and find a stimulation program that alleviates the patient's symptoms (e.g., pain). If external trial stimulation proves successful, the trial electrode array 17' is explanted, and a full IPG 10 and electrode array 17 are implanted as described above; if unsuccessful, the trial electrode array 17' is simply explanted.

Figure 5:
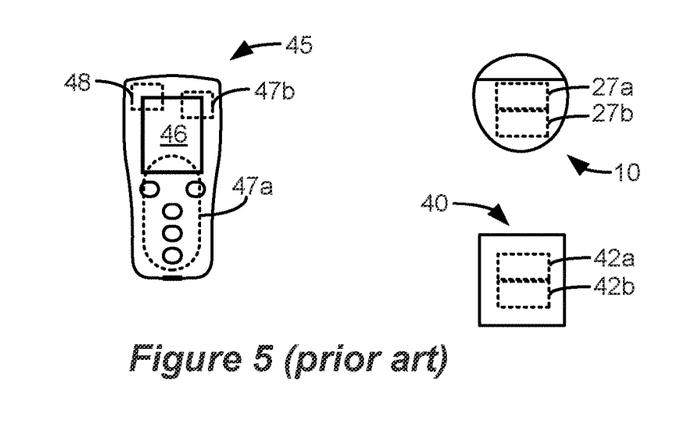
FIG. 5 shows various external devices capable of communicating with and programming stimulation in an IPG and ETS, in accordance with the prior art.

Like the IPG 10, the ETS 40 can include one or more antennas to enable bi-directional communications with external devices, explained further with respect to FIG. 5. Such antennas can include a near-field magnetic-induction coil antenna 42a, and/or a far-field RF antenna 42b, as described earlier. ETS 40 may also include stimulation circuitry able to form the stimulation pulses in accordance with a stimulation program, which circuitry may be similar or identical to the stimulation circuitry 28 present in the IPG 10. ETS 40 may also include a battery (not shown) for operational power.

FIG. 5 shows various external devices that can wirelessly communicate data with the IPG 10 and the ETS 40, including a patient hand-held external controller 45, and a clinician programmer 50. Both of devices 45 and 50 can be used to send a stimulation program to the IPG 10 or ETS 40—that is, to program their stimulation circuitries to produce pulses with a desired shape and timing described earlier. Both devices 45 and 50 may also be used to adjust one or more stimulation parameters of a stimulation program that the IPG 10 or ETS 40 is currently executing. Devices 45 and 50 may also receive information from the IPG 10 or ETS 40, such as various status information, etc.

External controller 45 can be as described in U.S. Patent Application Publication 2015/0080982 for example, and may comprise a dedicated controller configured to work with the IPG 10. External controller 45 may also comprise a general purpose mobile electronics device such as a mobile phone which has been programmed with a Medical Device Application (MDA) allowing it to work as a wireless controller for the IPG 10 or ETS 40, as described in U.S. Patent Application Publication 2015/0231402. External controller 45 includes a user interface, including means for entering commands (e.g., buttons or icons) and a display 46. The external controller 45's user interface enables a patient to adjust stimulation parameters, although it may have limited functionality when compared to the more-powerful clinician programmer 50, described shortly.

The external controller 45 can have one or more antennas capable of communicating with the IPG 10 and ETS 40. For example, the external controller 45 can have a near-field magnetic-induction coil antenna 47a capable of wirelessly communicating with the coil antenna 27a or 42a in the IPG 10 or ETS 40. The external controller 45 can also have a far-field RF antenna 47b capable of wirelessly communicating with the RF antenna 27b or 42b in the IPG 10 or ETS 40. The external controller 45 can also have controller circuitry 48 such as a microprocessor, microcomputer, an FPGA, other digital logic structures, etc., which is capable of executing instructions an electronic device. Controller circuitry 48 can for example receive patient adjustments to stimulation parameters, and create a stimulation program to be wirelessly transmitted to the IPG 10 or ETS 40.

Clinician programmer 50 is described further in U.S. Patent Application Publication 2015/0360038, and is only briefly explained here. The clinician programmer 50 can comprise a computing device 51, such as a desktop, laptop, or notebook computer, a tablet, a mobile smart phone, a Personal Data Assistant (PDA)-type mobile computing device, etc. In FIG. 5, computing device 51 is shown as a laptop computer that includes typical computer user interface means such as a screen 52, a mouse, a keyboard, speakers, a stylus, a printer, etc., not all of which are shown for convenience. Also shown in FIG. 5 are accessory devices for the clinician programmer 50 that are usually specific to its operation as a stimulation controller, such as a communication "wand" 54, and a joystick 58, which are coupleable to suitable ports on the computing device 51, such as USB ports 59 for example.

The antenna used in the clinician programmer 50 to communicate with the IPG 10 or ETS 40 can depend on the type of antennas included in those devices. If the patient's IPG 10 or ETS 40 includes a coil antenna 27a or 42a, wand 54 can likewise include a coil antenna 56a to establish near-filed magnetic-induction communications at small distances. In this instance, the wand 54 may be affixed in close proximity to the patient, such as by placing the wand 54 in a belt or holster wearable by the patient and proximate to the patient's IPG 10 or ETS 40. If the IPG 10 or ETS 40 includes an RF antenna 27b or 42b, the wand 54, the computing device 51, or both, can likewise include an RF antenna 56b to establish communication with the IPG 10 or ETS 40 at larger distances. (Wand 54 may not be necessary in this circumstance). The clinician programmer 50 can also establish communication with other devices and networks, such as the Internet, either wirelessly or via a wired link provided at an Ethernet or network port.

To program stimulation programs or stimulation parameters for the IPG 10 or ETS 40, the clinician interfaces with a clinician programmer graphical user interface (GUI) 64 provided on the display 52 of the computing device 51. As one skilled in the art understands, the GUI 64 can be rendered by execution of clinician programmer software 66 on the computing device 51, which software may be stored in the device's non-volatile memory 68. One skilled in the art will additionally recognize that execution of the clinician programmer software 66 in the computing device 51 can be facilitated by control circuitry 70 such as a microprocessor, microcomputer, an FPGA, other digital logic structures, etc., which is capable of executing programs in a computing device. Such control circuitry 70, in addition to executing the clinician programmer software 66 and rendering the GUI 64, can also enable communications via antennas 56a or 56b to communicate stimulation parameters chosen through the GUI 64 to the patient's IPG 10.

Figure 6:
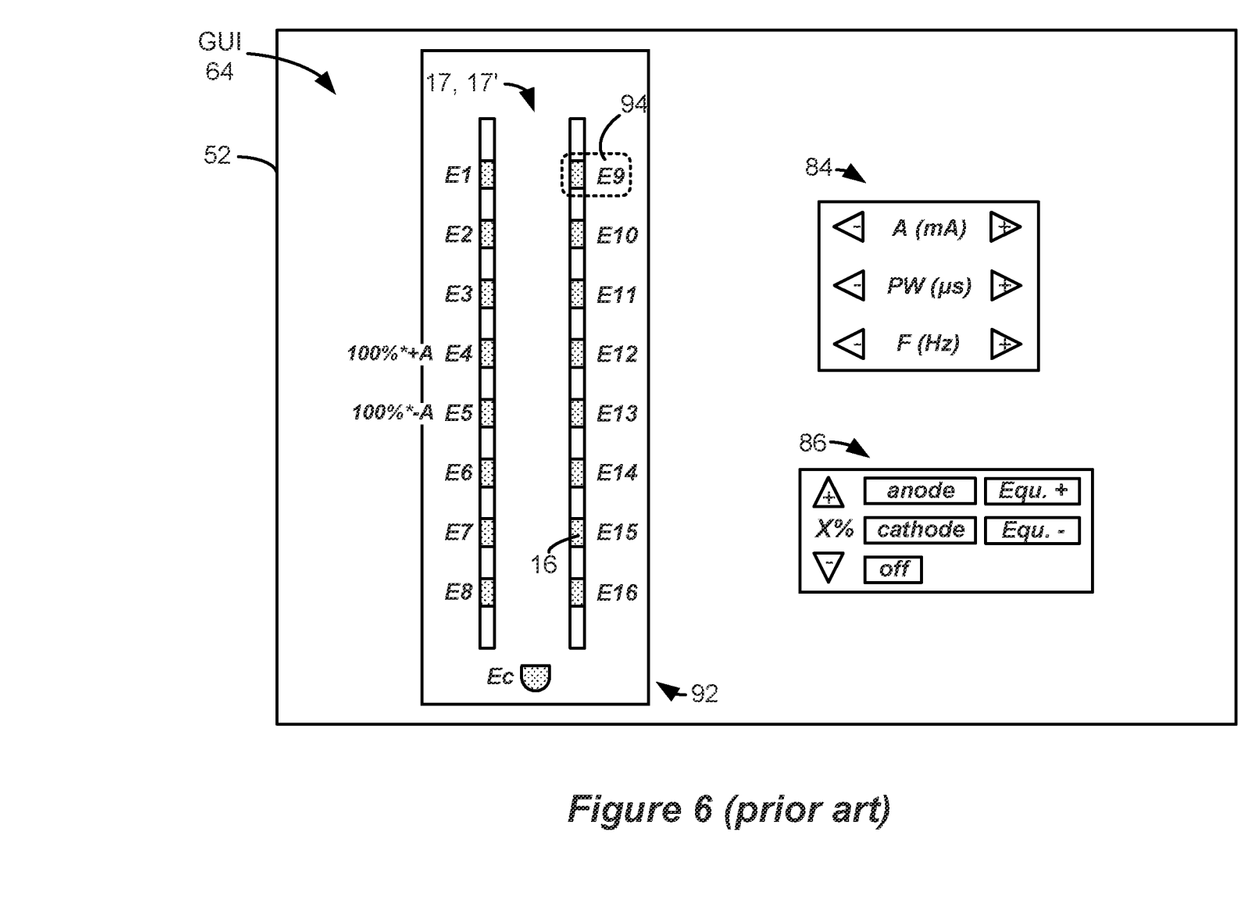
FIG. 6 shows a Graphical User Interface (GUI) of a clinician programmer external device for setting or adjusting stimulation parameters, in accordance with the prior art.

A portion of the GUI 64 is shown in one example in FIG. 6. One skilled in the art will understand that the particulars of the GUI 64 will depend on where clinician programmer software 66 is in its execution, which may depend on previous GUI selections the clinician has made. FIG. 6 shows the GUI 64 at a point allowing for the setting of stimulation parameters for the patient's IPG 10 or ETS 40. While GUI 64 is shown as operating in the clinician programmer 50, the user interface of the external controller 45 may provide similar functionality.

Shown to the right are interfaces where specific stimulation parameters can be defined for a stimulation program. Values for stimulation parameters relating to the shape of the waveform (A; in this example, current; PW; F) are shown in a waveform parameter interface 84, including buttons the clinician can use to increase or decrease these values. Stimulation parameters relating to the electrodes 16 (the active electrodes and their polarities), are made adjustable in an electrode parameter interface 86. Electrode parameters are also visible and can be manipulated in a leads interface 92 that displays the electrode array 17 (or 17') in generally their proper position with respect to each other, for example, on the left and right sides of the spinal column (only two leads are shown for simplicity). A cursor 94 (or other selection means such as a mouse pointer) can be used to select a particular electrode in the leads interface 92. Buttons in the electrode parameter interface 86 allow the selected electrode (including the case electrode, Ec) to be designated as an anode, a cathode, or off. The electrode parameter interface 86 further allows the relative strength of anodic or cathodic current of the selected electrode to be specified in terms of a percentage, X. This is particularly useful if more than one electrode is to act as an anode or cathode at a given time, as explained in the '038 Publication. In accordance with the example waveforms shown in FIGS. 2A and 2B, as shown in the leads interface 92, electrode E4 has been selected as the only anode to source current, and this electrode receives X=100% of the specified anodic current, +A. Likewise, electrode E5 has been selected as the only cathode to sink current, and this electrode receives X=100% of that cathodic current, −A. Again, more than one electrode can be selected to act as an anode or cathode at one time, with those electrodes sharing the anodic current +A or cathodic current −A. For example, electrodes E3 and E4 can both be selected to act as anode electrodes, with E3 receiving 30% of +A, and E4 receiving 70% of +A. GUI 64 can include other advanced options not shown as well, which for example allow for setting of a duty cycle (on/off time) for the stimulation pulses, setting a ramp-up time over which stimulation pulses will reach its programmed amplitude (A), options to specify the use of biphasic waveforms and/or passive charge recovery, etc.

SUMMARY

Disclosed herein is a method of providing electrical stimulation to a patient's spinal cord to treat pain in the patient using one or more electrode leads implantable in the patient's spinal column, wherein each electrode lead comprises a plurality of electrodes, the method comprising: determining a first perception threshold for stimulation at a first stimulation location and a second perception threshold for stimulation at a second stimulation location, determining first and second amplitudes using the first and second perception thresholds, and forming stimulation for the patient by using the plurality of electrodes to form a first pole at the first location and a second pole at the second location, wherein the first and second poles are each formed in first and second phases, wherein the first pole comprises a first polarity during the first phase and second polarity during the second phase, wherein the second pole comprises the second polarity during the first phase and the first polarity during the second phase, and wherein the first and second poles comprise the first amplitude during the first phase, and wherein the first and second poles comprise the second amplitude during the second phase. According to some embodiments, the perception threshold is defined with respect to a lowest amplitude of stimulation that the patient can feel or a highest amplitude of stimulation that the patient cannot feel. According to some embodiments, the first amplitude and the second amplitude are the same. According to some embodiments, the first amplitude and the second amplitude each comprise an average comprising the first perception threshold and the second perception threshold. According to some embodiments, the first amplitude and the second amplitudes are different. According to some embodiments, the first amplitude is determined based on the first perception threshold and the second amplitude is determined based on the second perception threshold. According to some embodiments, the first amplitude is a percentage of the first perception threshold and the second amplitude is a percentage of the second perception threshold. According to some embodiments, the first polarity is cathodic, and the second polarity is anodic. According to some embodiments, the first and second poles further comprise a third amplitude during the second phase. According to some embodiments, the third amplitude is 10 to 30% of the second amplitude. According to some embodiments, the first and second poles further comprise passive charge recovery during the second phase. According to some embodiments, the first and second poles are formed by activating a first one or more electrodes that in sum provide the first amplitude during the first phase and a second one or more electrodes that in sum provide the second amplitude during the second phase. According to some embodiments, the first and second phases are separated by an intra-pulse interval (IPI). According to some embodiments, the method further comprises optimizing the IPI. According to some embodiments, optimizing the IPI comprises determining an IPI-therapy model. According to some embodiments, the stimulation at the first pole recruits neural elements corresponding to a first one or more dermatomes during the first phase and the stimulation at the second pole recruits neural elements corresponding to a second one or more dermatomes during the second phase. According to some embodiments, the neural elements corresponding to the first one or more dermatomes comprises neural elements corresponding to a surround receptive field (SRF) of the first one or more dermatomes. According to some embodiments, the neural elements corresponding to the SRF of the first one or more dermatomes comprise dorsal column collaterals of Aβ-fiber afferents originating from the SRF of the first dermatome. According to some embodiments, the neural elements corresponding to the second one or more dermatomes comprises neural elements corresponding to a surround receptive field (SRF) of the second dermatome. According to some embodiments, the neural elements corresponding to the SRF of the second one or more dermatomes comprise dorsal column collaterals of Aβ-fiber afferents originating from the SRF of the second dermatome. According to some embodiments, the stimulation is below a perception threshold for the patient. According to some embodiments, pain relief washes in in a period of one hour or less after beginning to provide the stimulation. According to some embodiments, pain relief washes in in a period of ten minutes or less after beginning to provide the stimulation.

Also disclosed herein is a system for providing electrical stimulation to a patient's spinal cord to treat pain in the patient using one or more electrode leads implantable in the patient's spinal column, wherein each electrode lead comprises a plurality of electrodes, the system comprising: a neurostimulator that is connectable to the one or more electrode leads, and control circuitry configured to: determine a first perception threshold for stimulation at a first stimulation location and a second perception threshold for stimulation at a second stimulation location, determine first and second amplitudes using the first and second perception thresholds, and form stimulation for the patient by using the plurality of electrodes to form a first pole at the first location and a second pole at the second location, wherein the first and second poles are each formed in first and second phases, wherein the first pole comprises a first polarity during the first phase and second polarity during the second phase, wherein the second pole comprises the second polarity during the first phase and the first polarity during the second phase, and wherein the first and second poles comprise the first amplitude during the first phase, and wherein the first and second poles comprise the second amplitude during the second phase. According to some embodiments, the perception threshold is defined with respect to a lowest amplitude of stimulation that the patient can feel or a highest amplitude of stimulation that the patient cannot feel. According to some embodiments, the first amplitude and the second amplitude are the same. According to some embodiments, the first amplitude and the second amplitude each comprise an average comprising the first perception threshold and the second perception threshold. According to some embodiments, the first amplitude and the second amplitudes are different. According to some embodiments, the first amplitude is determined based on the first perception threshold and the second amplitude is determined based on the second perception threshold. According to some embodiments, the first amplitude is a percentage of the first perception threshold and the second amplitude is a percentage of the second perception threshold. According to some embodiments, the first polarity is cathodic, and the second polarity is anodic. According to some embodiments, the first and second poles further comprise a third amplitude during the second phase. According to some embodiments, the third amplitude is 10 to 30% of the second amplitude. According to some embodiments, the first and second poles further comprise passive charge recovery during the second phase. According to some embodiments, the first and second poles are formed by activating a first one or more electrodes that in sum provide the first amplitude during the first phase and a second one or more electrodes that in sum provide the second amplitude during the second phase. According to some embodiments, the first and second phases are separated by an intra-pulse interval (IPI). According to some embodiments, the control circuitry is configured to determine an IPI-therapy model correlating the IPI with pain relief. According to some embodiments, the control circuitry is configured to optimize the IPI using the IPI-therapy model. According to some embodiments, the stimulation at the first pole is configured to recruit neural elements corresponding to a first one or more dermatomes during the first phase and the stimulation at the second pole is configured to recruit neural elements corresponding to a second one or more dermatomes during the second phase. According to some embodiments, the neural elements corresponding to the first one or more dermatomes comprises neural elements corresponding to a surround receptive field (SRF) of the first one or more dermatomes. According to some embodiments, the neural elements corresponding to the SRF of the first one or more dermatomes comprise dorsal column collaterals of Aβ-fiber afferents originating from the SRF of the first dermatome. According to some embodiments, the neural elements corresponding to the second one or more dermatomes comprises neural elements corresponding to a surround receptive field (SRF) of the second dermatome. According to some embodiments, the neural elements corresponding to the SRF of the second one or more dermatomes comprise dorsal column collaterals of Aβ-fiber afferents originating from the SRF of the second dermatome. According to some embodiments, the stimulation is below a perception threshold for the patient.

The invention may also reside in the form of a programed external device (via its control circuitry) for carrying out the above methods, a programmed IPG or ETS (via its control circuitry) for carrying out the above method, a system including a programmed external device and IPG or ETS for carrying out the above methods, or as a computer readable media for carrying out the above methods stored in an external device or IPG or ETS.

DETAILED DESCRIPTION

While Spinal Cord Stimulation (SCS) therapy can be an effective means of alleviating a patient's pain, such stimulation can also cause paresthesia. Paresthesia is a sensation such as tingling, prickling, heat, cold, etc. that can accompany SCS therapy. Generally, the effects of paresthesia are mild, or at least are not overly concerning to a patient. Moreover, paresthesia is generally a reasonable tradeoff for a patient whose chronic pain has now been brought under control by SCS therapy. Some patients even find paresthesia comfortable and soothing. SCS therapy that causes paresthesia may be referred to as supra-perception therapy. Nonetheless, at least for some patients, SCS therapy would ideally provide complete pain relief without paresthesia—what is often referred to as "sub-perception" or sub-threshold therapy, i.e., therapy that a patient cannot feel.

Figures 7, 8, 9:
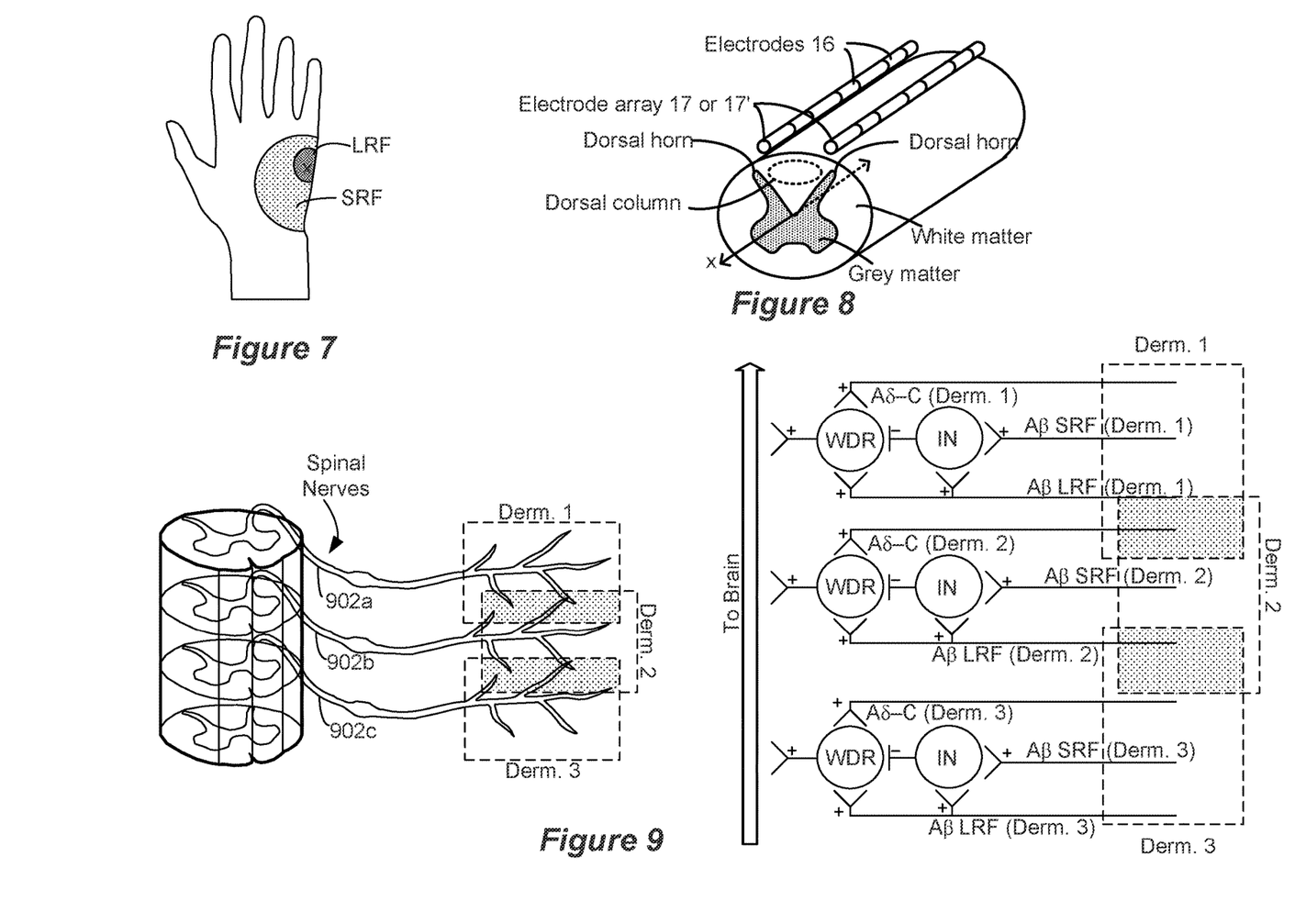
FIG. 7 shows a local receptive field (LRF) and surround receptive field (SRF) relative to a locus of pain.
FIG. 8 shows electrodes configured with respect to a section of spinal cord.
FIG. 9 shows a innervation of three overlapping dermatomes and a network model for relevant neural elements in the spinal cord.

Fast acting sub-perception therapy may be facilitated by exploiting a mechanism of action (MOA) that involves using SCS to activate neural elements involved in surround inhibition. FIG. 7 shows an illustration of a patient's hand. Note that the patient's hand is illustrated as an example of a peripheral location at which the patient might experience pain, but the disclosure relates to any peripheral location on the patient's body. Assume that the patient experiences pain at a location (i.e., a locus) marked by the "x" in a region of their hand, referred to herein as a local receptive field (LRF). The illustration of FIG. 7 also shows an area surrounding the LRF, referred to herein as a surrounding receptive field (SRF). Afferent nerve fibers from each of the LRF and the SRF travel through peripheral nerves to the spinal cord. The fibers from the LRF and SRF may participate differently from one another in various networks in the dorsal horn. See, e.g., Hillman and Wall, "Inhibitory and Excitatory Factors Influencing the Receptive Fields of Lamina 5 Spinal Cord Cells," Exp. Brain Res. 9, 284-306, (1969); and Zhang, et al., "Modeling effects of spinal cord stimulation on wide-dynamic range dorsal horn neurons: influence of stimulation frequency and GABAergic inhibition," J. Neurophysiol. 115: 552-67, (2014). It has been found that delivering electrical stimulation to dorsal column collaterals of Aβ-fiber afferents originating only from the LRF does not always provide optimum pain relief. However, additionally delivering stimulation to dorsal column collaterals of Aβ-fiber afferents originating from the SRF provides pain relief (with respect to pain centered in the LRF) and can provide fast onset of sub-perception therapy. Accordingly, aspects of the disclosure relate to methods and systems for providing electrical stimulation that activates neural elements of the spinal cord corresponding to the SRF, for example, dorsal column collaterals of Aβ-fiber afferents originating from the SRF. According to some embodiments, pain relief may wash in within a period of one hour or less after beginning the therapeutic stimulation. According to some embodiments, pain relief may wash in within a period of ten minutes or less after beginning the therapeutic stimulation. According to some embodiments the pain relief may be instantaneous.

FIG. 8 shows a typical transverse section of the spinal cord showing the central "butterfly" shaped central area of gray matter (neuronal cell bodies) substantially surrounded by an ellipse-shaped outer area of white matter (myelinated axons). The dorsal horns are the dorsal portions of the "butterfly" shaped central area of gray matter, which includes neuronal cell terminals, neuronal cell bodies, dendrites, and axons. As mentioned above, embodiments of the disclosed methods seek to stimulate dorsal column fibers that run in the white matter along the longitudinal axis of the spinal cord. Specifically, electrodes 16 are used to stimulate Aβ-fiber afferents originating from the LRF and/or SRF.

The left side of FIG. 9 illustrates a section of the spinal cord showing three nerves 902a-c, which ultimately innervate three dermatomes (Derms. 1-3). Notice that there are areas where dermatome 1 overlaps with dermatome 2 and where dermatome 2 overlaps with dermatome 3. The right side of FIG. 9 illustrates a neural network representation of nociceptive processing relative to the three dermatomes as would occur in the spinal cord. The network representation is similar to those described in the Hillman and Zhang articles referenced above. Each dermatome is associated with Aδ and/or C fibers, which, when excited, positively excite wide dynamic range (WDR) projection neurons in the dorsal horn, causing pain/sensation signals to be transmitted to the brain. Each dermatome is also associated with Aβ fibers that are associated with the local receptive field (LRF) for that dermatome. The LRF Aβ fibers project to the WDR neurons, facilitating the transmission of pain/sensation signals to the brain, but they also project to inhibitory interneurons (IN), which down-modulate the activity of the WDR, decreasing the pain signals. Accordingly, when SCS electrical stimulation stimulates dorsal column collaterals of LRF Aβ fibers, some pain relief may be achieved because of the inhibitory network involving the IN. But that pain relief may not be optimal, because the LRF also asserts positive excitation of the WDR. Each dermatome is also associated with surround receptive field (SRF) Aβ fibers. The SRF Aβ fibers project to the inhibitory IN. Accordingly, stimulation of the SRF Aβ fibers for a dermatome decrease the sensation of pain in that dermatome. Embodiments of the disclosed methods and systems seek to provide stimulation to dorsal column collaterals of SRF neurons.

Figure 10:
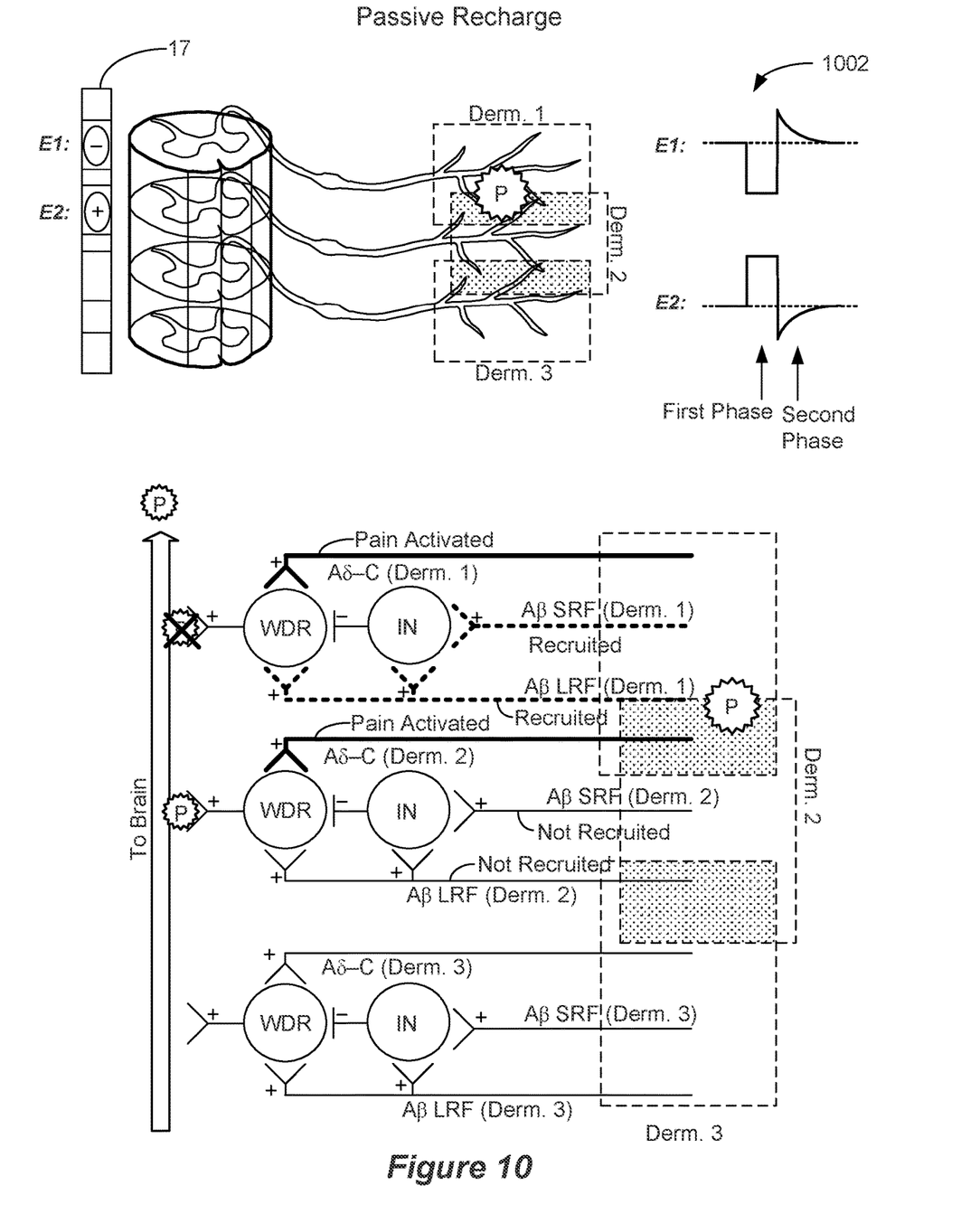
FIG. 10 illustrates treatment of pain in overlapping dermatomes using passive charge recovery.

FIG. 10 illustrates a situation where the locus of a patient's pain is situated at a location where two dermatomes (Derms. 1 and 2, in the illustrated example) overlap. Notice that the pain locus is completely contained within dermatome 1, but is also contained within a portion of dermatome 2. So, the Aδ and/or C fibers of both dermatomes 1 and 2 are activated. An electrode lead 17 is configured to provide electrical stimulation to the dorsal column of the spinal cord. Note that the electrode lead would be implanted near the dorsal columns, as illustrated in FIG. 8, but is shown at a lateral side of the spinal column here just for illustration. Assume that the electrode lead is positioned so that stimulation using the electrode E1 as a stimulating pole can recruit collaterals of the LRF and SRF Aβ fibers corresponding to dermatome 1. Electrical stimulation using passive charge recovery is applied to the spinal cord, using an electrode E1 as a cathode and an electrode E2 as an anode. Note that typically in SCS cathodic stimulation is considered the most therapeutically effective because it depolarizes the target neural elements, whereas anodic stimulation hyperpolarizes them. So, in FIG. 10, the cathodic pulse at E1 may be considered the therapeutic pulse; the anodic pulse at E2 is primarily used to draw the current out of the tissue. Note that there are some therapy paradigms in which anodic stimulation is therapeutic, but for the purposes of this discussion we are considering the cathodic (depolarizing) pulse as the therapeutically effective part of the waveform. FIG. 10 illustrates the phases of waveforms 1002 provided at E1 and E2. The first phases of the waveforms are actively driven (cathodic in E1, anodic in E2) and the second phase is passive recovery, as explained above, with respect to FIG. 2B.

The bottom of FIG. 10 illustrates a neural network model corresponding to the situation described above. The Aδ and C fibers corresponding to both dermatomes 1 and 2 are active (as illustrated by the bold line) because the pain locus is contained within both of those dermatomes. The cathodic stimulation provided at the electrode E1 recruits collaterals of the LRF and SRF fibers corresponding to dermatome 1 (as illustrated by the dashed line). Accordingly, the pain signals from dermatome 1 are blocked (notice that the pain signal "P" corresponding to dermatome 1 is "x-ed out"). If the stimulation is supra-perception, the patient will perceive paresthesia that covers the locus of their pain. But notice that the stimulation does not recruit the collaterals of the LRF and SRF Aβ fibers corresponding to dermatome 2. So, the stimulation does not block the pain arising from the Aδ and C fibers corresponding to that dermatome. Thus, the patient may still perceive some pain, even though the paresthesia covers the site of their pain. Note that E2 may be located proximal to collaterals of the LRF and SRF Aβ fibers corresponding to dermatome 2, but since only anodic stimulation is provided at that electrode no activation of those fibers is achieved.

In the example illustrated in FIG. 10, the stimulation fails to provide optimum pain relief because the passive recharge stimulation creates only a single stimulating pole and depolarizes only a single location (i.e., a single center point of stimulation (CPS)), which is located at the cathode. In the illustrated example, that pole does not recruit the SRF neural targets for all of the relevant dermatomes (namely, it doesn't recruit targets for dermatome 2). Embodiments of the presently disclosed methods and systems use active recharge and take advantage of the fact that the biphasic waveforms used during active recharge effectively provide two stimulating poles-one stimulating pole that is depolarizing during the first phase and one stimulating pole that is depolarizing during the second phase.

Figure 11:
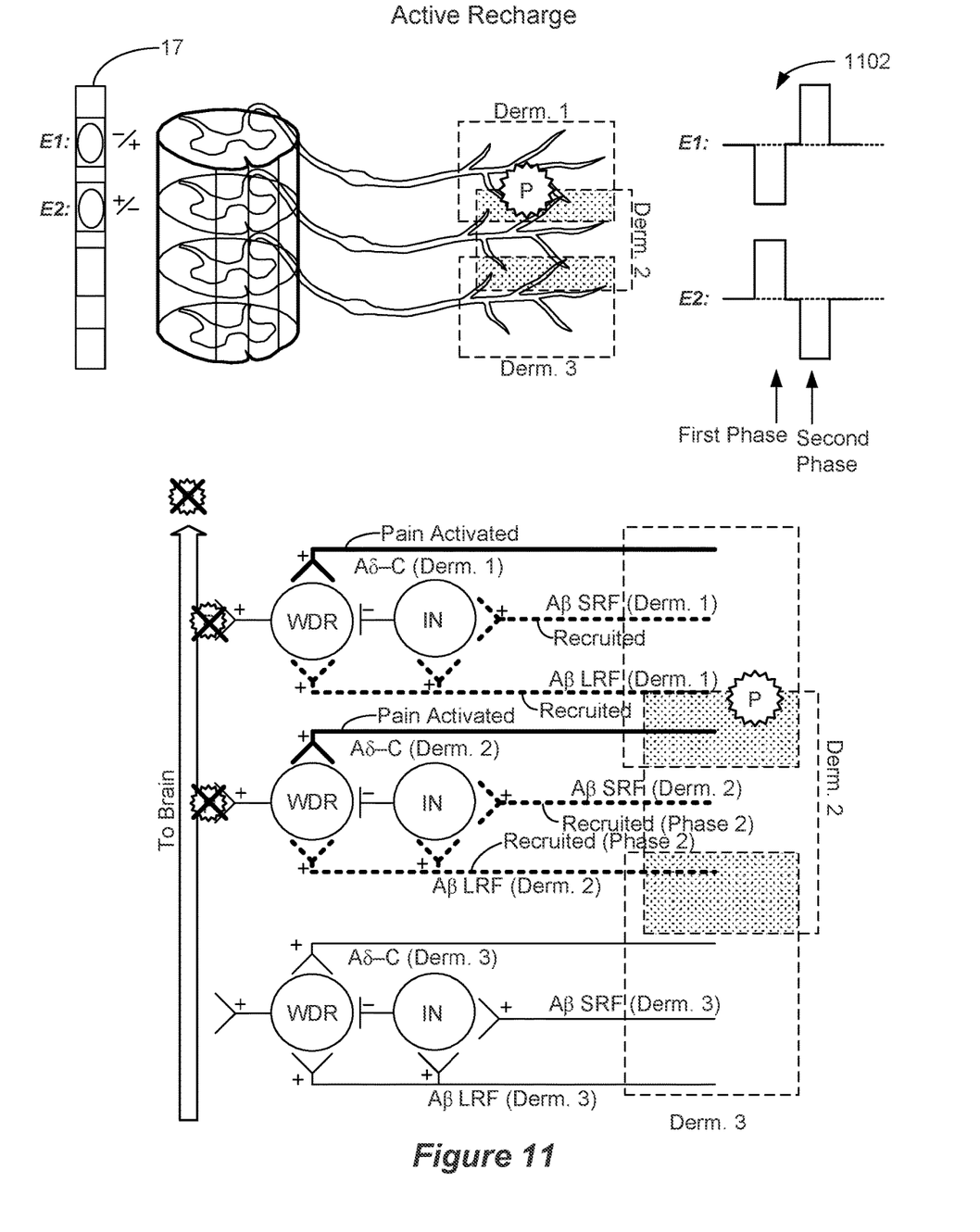
FIG. 11 illustrates treatment of pain in overlapping dermatomes using active charge recovery.

FIG. 11 illustrates an example of using active recharge SCS to treat pain that is located in an overlap of two dermatomes. As shown in the waveform 1102, the electrode E1 is cathodic during the first phase of the pulse and the electrode E2 is anodic. Thus, the first phase of the pulse creates a first depolarizing (or negative) pole at E1. But during the second phase of the pulse E2 becomes cathodic and E1 becomes anodic. So, the second phase creates a second depolarizing (or negative)pole (located at E2) that may be capable of recruiting additional neural elements that were not recruited during the first phase. Specifically, if the correct electrodes are selected, the stimulating pole created during the second phase of the pulse may be configured to recruit the collaterals of the LRF and SRF Aβ fibers corresponding to dermatome 2, as show in the illustration. When the collaterals of the LRF and SRF Aβ fibers corresponding to dermatome 2 are recruited, the pain arising from the WDR projection neurons of both dermatomes may be down-modulated, achieving better pain relief for the patient. In other words, the second phase (i.e., the charge recovery phase) acts as a second therapeutic stimulation in addition to just recovering charge.

Figure 12:
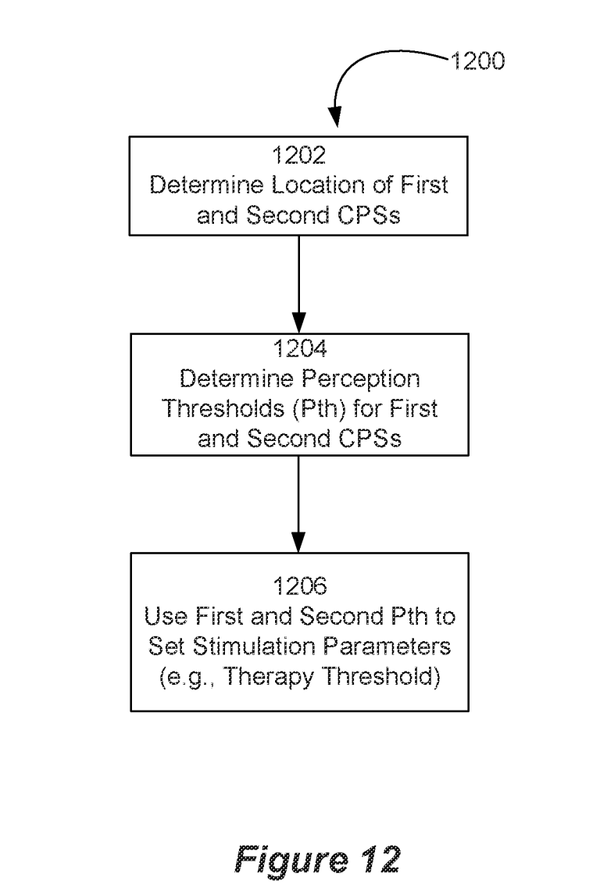
FIG. 12 shows an embodiment of an algorithm for independently configuring amplitudes of two phases of a biphasic stimulation waveform.

Aspects of this disclosure concern optimizing the biphasic stimulation waveform so that both phases of the stimulation pulse are therapeutically effective, particularly for sub-perception SCS therapy. FIG. 12 illustrates an algorithm 1200 embodying aspects of the disclosure. At step 1202 locations for the first and second CPSs are determined. This amounts to determining electrode pole configurations for providing cathodic stimulation at the optimum first CPS during the first phase of the pulse and at the second CPS during the second phase of the pulse. As used herein, the term "electrode pole configuration" refers to which electrodes are active at a given time and how current is proportioned among the active electrodes. In the example illustrated in FIG. 11 the first stimulating pole coincides with the location of the electrode E1 and the second stimulating pole coincides with the location of the electrode E2. However, the poles do not necessarily have to correspond to the locations of physical electrodes. For example, cathodic current may be split between multiple electrodes to provide a "virtual cathode" or "virtual pole" located between locations of physical electrodes. The current amplitude of the pole is formed by activating one or more electrodes that, in sum, provide the amplitude at the pole location. Likewise, anodic current may be split between multiple electrodes to provide a "virtual anode." The process of determining which electrodes to use for providing stimulation (i.e., determining optimum poles) is sometimes referred to as "sweet spot" searching. Various techniques for sweet spot searching are described in the art and is not described here in detail. See, e.g., U.S. Patent Pub. No. 2020/0147390.

Once pole configurations for the first and second CPSs are determined, perception thresholds for each of the CPSs are determined (step 1204). Embodiments of the disclosed methods and systems concern sub-perception stimulation, which, as explained above, involves providing therapeutic stimulation that is below the patient's perception threshold (Pth). To program such stimulation, it is necessary to determine the stimulation intensity that corresponds to the perception threshold. Typically, prior art methods involved determining only a single Pth for a stimulation waveform, regardless of whether the waveform used passive or active recharge. In other words, even if a biphasic waveform, such as waveform 1102 (FIG. 11) was used, only a single Pth value would be determined for that waveform. The inventors have realized that the different neural elements (e.g., collaterals of the LRF and SRF Aβ fibers) recruited by the two different stimulating poles associated with the two phases of a biphasic waveform may have different morphologies and membrane excitabilities. Accordingly, each CPS (and each phase of the biphasic pulse) may be associated with a different Pth.

According to some embodiments, the Pth for each of the CPSs are measured independently. This is to better leverage the recruitment for each phase. For this discussion, the pole that is cathodic during the first phase of the pulse is denoted as stimulating pole A and it provides stimulation at a location CPSA. Stimulation at CPSA may be associated with a perception threshold PthA. The pole that is cathodic during the second phase of the pulse is denoted as stimulating pole B and provides stimulation at a location CPSB, is associated with a perception threshold PthB. PthA can be measured by providing cathodic stimulation at CPSA and using passive recharge. The stimulation intensity can be adjusted (e.g., starting at a low value and increasing the stimulation amplitude) to the point that the patient first reports feeling paresthesia. Alternatively, the perception threshold may be measured by sensing physiological responses (such as evoked compound action potentials (ECAPs), electromyography (EMG) responses, or the like). The process can be repeated using stimulating pole B for cathodic stimulation and using passive recharge to determine PthB. It may also be helpful to measure a perception threshold for the active recharge waveform, i.e., when the cathode is at CPSA and the anode is at CPSB and vice-versa. That perception threshold is denoted herein as PthC.

At step 1206, once the PthA and PthB values are determined, those values can be used to set stimulation parameters for the patient's therapy. According to some embodiments, a therapy threshold (PthT) may be determined, which may be considered as the highest intensity at which stimulation may be provided and still be sub-perception. According to some embodiments, PthT may be determined as a function of the determined PthA and PthB values. For example, the PthT may be an average of the PthA and PthB values. Alternatively, the therapy threshold PthT may be calculated as an average of PthA, PthB, and PthC. Generally, any function that combines PthA, PthB, and optionally PthC may be used to determine the therapy threshold PthT, depending on the specifics of the therapy.

The above examples assume that the intensities (amplitudes) of the first and second phases of the biphasic pulses are equal. In other words, the biphasic waveforms are symmetric. However, some embodiments described herein involve using different amplitudes and possibly different pulse widths for each phase. In other words, some embodiments described herein use asymmetric biphasic waveforms. That way, the amplitude of each phase can be tailored for the perception threshold associated with its corresponding CPS. Referring to the waveforms illustrated in FIG. 13, assume that a first center-point of stimulation CPSA has a higher perception threshold (PthA) than a second center-point of stimulation CPSB (having a perception threshold of PthB). In the biphasic waveforms illustrated in FIG. 13, the electrode E1 is cathodic first, and is therefore the stimulating pole first. During the first phase E1 issues cathodic current having an amplitude of current I1 and a pulse-width of PW1 while the electrode E2 issues anodic current having the same amplitude (I1) and pulse-width (PW1). The first phase of the waveform stimulates at the center-point of stimulation CPSA. The magnitude of the current I1 can be determined based on the perception threshold at the CPSA (i.e., based on PthA). For example, the current I1 may be some fraction of the perception threshold current, for example 50% of the threshold current. During the second phase E2 is the stimulating pole and issues cathodic current having an amplitude of I2 and a pulse-width of PW2 while the electrode E1 issues anodic current having the same amplitude (I2) and pulse-width (PW2). The second phase of the waveform stimulates at a center-point of stimulation CPSB. The magnitude of the current I2 can be determined based on the perception threshold at the CPSB (i.e., based on PthB). Notice that I2 is less than I1. That is because PthB is less than PthA in this example. Note that the first and second phases of the waveforms are separated by in intra-pulse interval (IPI). Aspects of the IPI are discussed in more detail below.

Waveforms having phases with different amplitudes provide the flexibility of choosing amplitudes for each phase that is tailored to the perception threshold of the neural elements recruited during that phase. But according to some embodiments such waveforms must meet certain constraints. For example, generally the charge injected during the first phase must equal the charge recovered during the second phase. In other words, in the waveforms illustrated in FIG. 13, C1 must equal the sum of C2 plus C3. For square waveforms, like C1 and C2 of FIG. 13, the charge is simply the amplitude multiplied by the pulse width. So C1 is equal to I1×PW1 and C2 is equal to I2×PW2. The charge C3 is equal to the area under the decaying curve.

Figure 13:
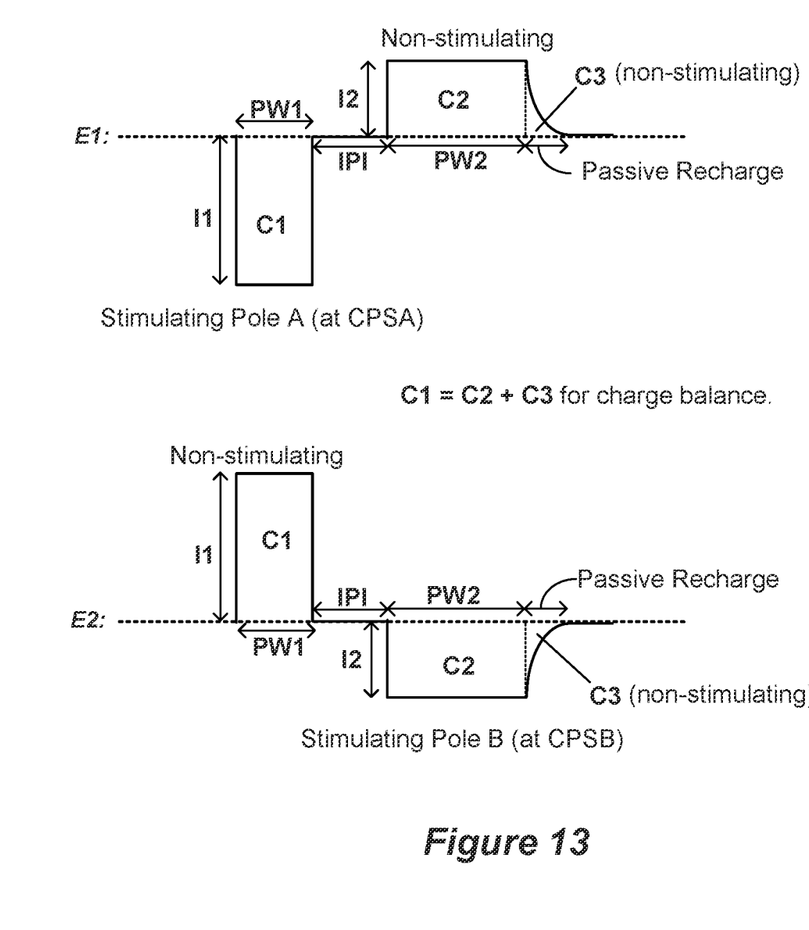
FIG. 13 shows embodiments of an asymmetric biphasic waveform including passive charge recovery.

Programming waveforms having phases with different amplitudes like those shown in FIG. 13 involves first determining perception thresholds for the two targeted CPSs, as described above. That allows setting of the stimulation amplitudes (I1 for CPSA and I2 for CPSB) for each of the phases. As mentioned above, according to some embodiments, the amplitudes I1 and I2 may be set aa fractions of the respective perception thresholds. Pulse widths (PWs) for each of the stimulating phases may also be determined. The pulse width for each phase may be different. According to some embodiments, the pulse width of each pulse may be chosen based on the particular targeted neural elements to be recruited by that phase. Typically, the phase that has the largest charge (C) value, i.e., the largest product of amplitude and pulse width (I×PW) should be chosen as the first stimulating phase. In FIG. 13, C1 (i.e., I1×PW1) is greater than C2 (i.e., I2×PW2), so the C1 phase is programmed as the first phase. The C2 phase recovers most of the injected charge, but since C2 is less than C1 some charge still remains unrecovered. That remaining charge can be recovered using passive recharge (i.e., C3), which is non-stimulating.

Figure 14:
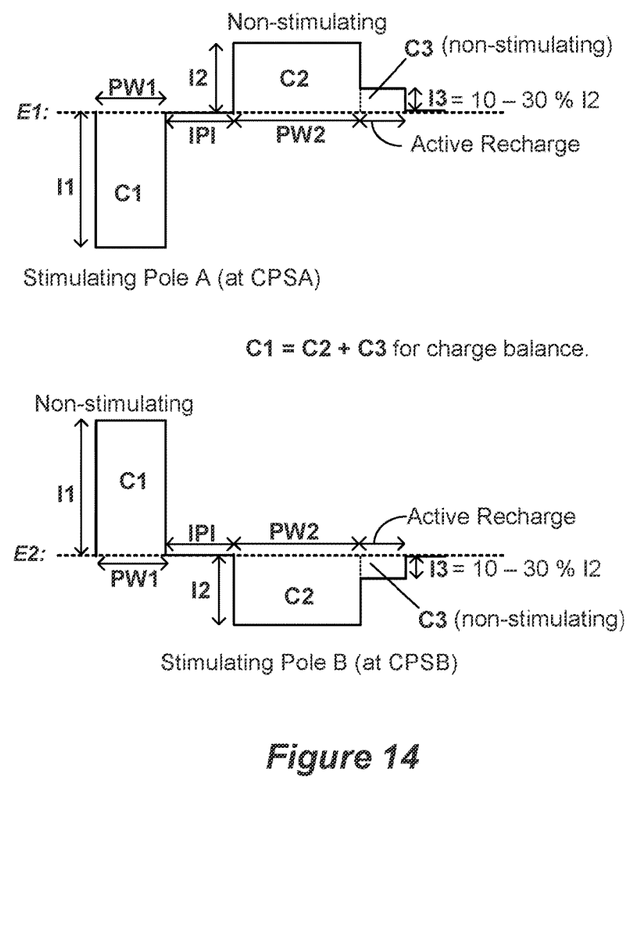
FIG. 14 shows embodiments of an asymmetric biphasic waveform including active charge recovery.

FIG. 14 shows another pair of biphasic waveforms wherein the two phases have different amplitudes. The waveforms shown in FIG. 14 use actively driven recharge following the second phase to recover the remaining charge (C3). The recharge amplitude I3 is chosen to be non-stimulating and is therefore below the rheobase intensity for the neural elements targeted in the second phase. According to some embodiments, the amplitude I3 may be about 10 to about 30 percent of I2.

Figure 15:
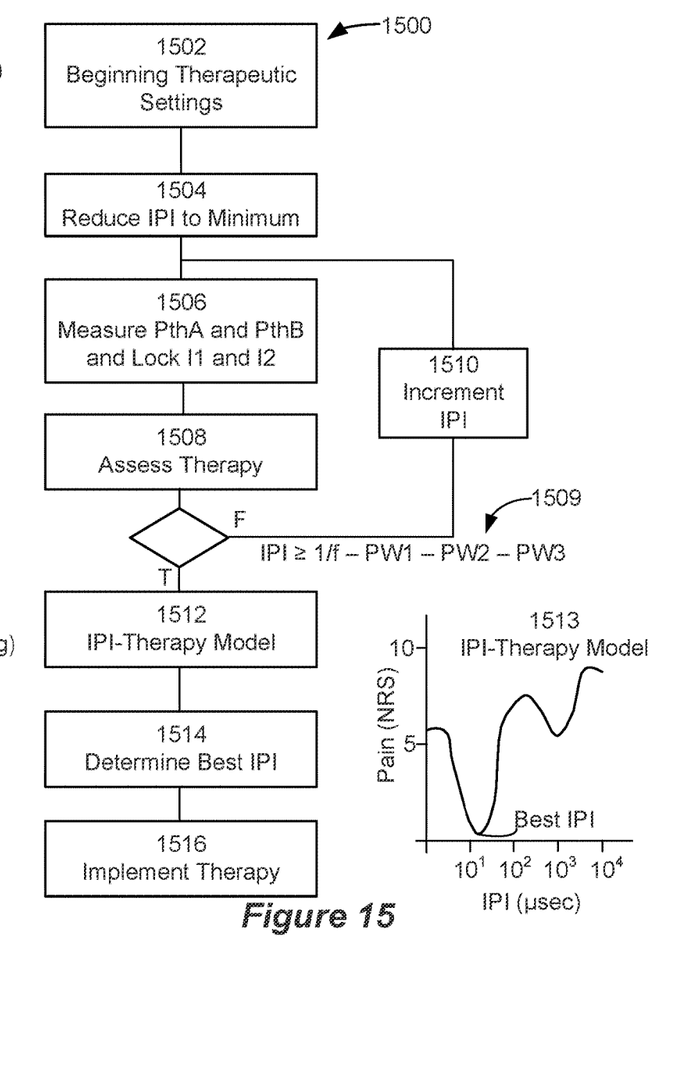
FIG. 15 shows an embodiment of an algorithm for configuring biphasic waveforms for optimal sub-perception therapy, including optimizing an intra-pulse interval (IPI).

As mentioned above, the phases of the biphasic waveforms described herein may be separated by an intra-pulse interval (IPI), as shown in FIGS. 13 and 14. The inventors have realized that the IPI may be optimized to therapeutic effect. FIG. 15 illustrates an embodiment of an algorithm for defining waveforms having optimal target recruitment, stimulation dosing, and temporal focusing. The algorithm includes optimizing the IPI. The algorithm may begin by applying stimulation using a base or beginning set of therapeutic stimulation parameters (Step 1502). According to some embodiments, the beginning therapeutic stimulation parameters may be selected according to methods described in International Application Publication Number WO 2021/178105 ("the '105 Publication), the entire contents of which are incorporated herein by reference. For example, sweet-spot searching as described above may be used to determine electrode configurations for providing stimulation having stimulating poles that are effective at covering the patient's pain. Various combinations of stimulation parameters, such as frequency, amplitude, and pulse-width may be adjusted/optimized, as described in the '105 Publication, to provide beginning therapeutic settings. According to some embodiments, the beginning therapeutic settings comprise symmetric biphasic pulses wherein the phases are separated by an intra-pulse interval (IPI). The IPI may have a default value, for example, about 100 μs.

At step 1504 the IPI is reduced to a minimum value, for example, about 1 μs. At step 1506 perception thresholds for the two CPSs (i.e., PthA and PthB, as discussed above) are determined. Techniques for determining PthA and PthB are described above. As described above, the stimulation amplitudes for the two phases (I1 and I2) can be set based on the measured perception thresholds. At step 1508, therapy is assessed using the constructed waveform. Assessing therapy may involve applying the therapy and having the patient rank their pain level, using a numeric rating scale (NRS) for example. Therapy may also be assessed using measurements, such as ECAP measurements, EMG, EEG, and the like.

One goal of the algorithm 1500 is to determine a relationship between the IPI and the efficacy of the therapy. Accordingly, the IPI is can be incrementally increased (step 1510) and the steps of 1506 and 1508 can be repeated using different IPIs. Note that according to some embodiments, the PthA and PthB may not need to be reassessed with each new IPI. Note also that the amount that the IPI can be increased is limited by the frequency and pulse widths of the pulses of the waveforms. According to some embodiments, the IPI may be incremented as long as the equation 1509 is false. Once the equation is met, the algorithm may proceed to the next step.

At step 1512 the algorithm uses the therapy assessments determined for each of the IPIs to generate an IPI-therapy model 1513. According to some embodiments, the IPI-therapy model 1513 is a mathematical relationship relating one or more aspects of the patient's therapy, such as their pain level, to the IPI. For example, the mathematical relationship may be a function, such as a polynomial functions, a spline function, or the like. Once the IPI-therapy model is generated it can be used to select the best IPI for ongoing therapy (Step 1514). For example, this may be done by determining the IPI at which the patient's pain rating is minimized. According to some embodiments, the algorithm may determine an IPI value at which the first derivative the IPI-therapy model function is zero and at which the second derivative is positive. Once the best IPI is identified, therapeutic waveforms having the best IPI can be implemented for the patient's ongoing therapy (step 1516).

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method of providing electrical stimulation to a patient's spinal cord to treat pain in the patient using one or more electrode leads implantable in the patient's spinal column, wherein each electrode lead comprises a plurality of electrodes, the method comprising:
   determining a first perception threshold for stimulation at a first stimulation location and a second perception threshold for stimulation at a second stimulation location,
   determining a first amplitude based on the first perception threshold and a second amplitude based on the second perception threshold, and
   forming stimulation for the patient by using the plurality of electrodes to form a first pole at the first location and a second pole at the second location,
      wherein the first and second poles are each formed in first and second phases,
      wherein the first pole comprises a first polarity during the first phase and second polarity during the second phase,
      wherein the second pole comprises the second polarity during the first phase and the first polarity during the second phase, and
      wherein the first and second poles comprise the first amplitude during the first phase, and
      wherein the first and second poles comprise the second amplitude during the second phase.

2. The method of claim 1, wherein the perception threshold is defined with respect to a lowest amplitude of stimulation that the patient can feel or a highest amplitude of stimulation that the patient cannot feel.

3. The method of claim 1, wherein the first amplitude and the second amplitude are the same.

4. The method of claim 3, wherein the first amplitude and the second amplitude each comprise an average of the first perception threshold and the second perception threshold.

5. The method of claim 1, wherein the first amplitude and the second amplitudes are different.

6. The method of claim 5, wherein the first amplitude is determined based on the first perception threshold and the second amplitude is determined based on the second perception threshold.

7. The method of claim 1, wherein the first and second poles further comprise a third amplitude during the second phase.

8. The method of claim 7, wherein the third amplitude is 10 to 30% of the second amplitude.

9. The method of claim 1, wherein the first and second poles further comprise passive charge recovery during the second phase.

10. The method of claim 1, wherein the first and second poles are formed by activating a first one or more electrodes that in sum provide the first amplitude during the first phase and a second one or more electrodes that in sum provide the second amplitude during the second phase.

11. The method of claim 1, wherein the first and second phases are separated by an intra-pulse interval (IPI).

12. The method of claim 11, wherein the method further comprises optimizing the IPI using an IPI-therapy model.

13. The method of claim 1, further comprising selecting the first stimulation location to recruit neural elements corresponding to a first one or more dermatomes during the first phase and selecting the second stimulation location to recruit neural elements corresponding to a second one or more dermatomes during the second phase.

14. The method of claim 13, wherein the neural elements corresponding to the first one or more dermatomes comprises neural elements corresponding to a surround receptive field (SRF) of the first one or more dermatomes.

15. The method of claim 14, wherein the neural elements corresponding to the SRF of the first one or more dermatomes comprise dorsal column collaterals of AB-fiber afferents originating from the SRF of the first dermatome.

16. The method of claim 13, wherein the neural elements corresponding to the second one or more dermatomes comprises neural elements corresponding to a surround receptive field (SRF) of the second dermatome.

17. The method of claim 16, wherein the neural elements corresponding to the SRF of the second one or more dermatomes comprise dorsal column collaterals of AB-fiber afferents originating from the SRF of the second dermatome.

18. The method of claim 1, wherein the stimulation is below a perception threshold for the patient.

* * * * *